(12) United States Patent
He et al.

(10) Patent No.: US 10,813,754 B2
(45) Date of Patent: Oct. 27, 2020

(54) DRIVING HANDLE FOR DELIVERING IMPLANT, AND DELIVERY SYSTEM

(71) Applicant: SHANGHAI MICROPORT CARDIOFLOW MEDTECH CO., LTD., Shanghai (CN)

(72) Inventors: Zhixiu He, Shanghai (CN); Xiang Liu, Shanghai (CN); Baozhu Gui, Shanghai (CN); Yu Li, Shanghai (CN); Haishan Wang, Shanghai (CN); Mingming Wu, Shanghai (CN); Yunlei Wang, Shanghai (CN)

(73) Assignee: Shanghai Microport Cardioflow Medtech Co., Ltd., Shanghai (CN)

( * ) Notice: Subject to any disclaimer, the term of this patent is extended or adjusted under 35 U.S.C. 154(b) by 273 days.

(21) Appl. No.: 15/568,240

(22) PCT Filed: Apr. 27, 2016

(86) PCT No.: PCT/CN2016/080347
§ 371 (c)(1),
(2) Date: Oct. 20, 2017

(87) PCT Pub. No.: WO2016/173495
PCT Pub. Date: Nov. 3, 2016

(65) Prior Publication Data
US 2018/0110621 A1  Apr. 26, 2018

(30) Foreign Application Priority Data

Apr. 29, 2015  (CN) .......................... 2015 1 0213801

(51) Int. Cl.
*A61F 2/24*  (2006.01)
*A61F 2/95*  (2013.01)
(Continued)

(52) U.S. Cl.
CPC .............. *A61F 2/2436* (2013.01); *A61F 2/24* (2013.01); *A61F 2/95* (2013.01); *A61F 2/966* (2013.01); *A61F 2/4603* (2013.01); *A61F 2/9517* (2020.05)

(58) Field of Classification Search
CPC .. A61F 2/24; A61F 2/2436; A61F 2/95; A61F 2/966; A61F 2002/4623; A61F 2002/9517
See application file for complete search history.

(56) References Cited

U.S. PATENT DOCUMENTS 5,672,153 A * 9/1997 Lax .................... A61B 10/0233
604/22
2005/0107862 A1* 5/2005 Ohlenschlaeger ........ A61F 2/07
623/1.11

(Continued)

FOREIGN PATENT DOCUMENTS

CN  1961847 A  5/2007
CN  101553190 A  10/2009

(Continued)

*Primary Examiner* — Jocelin C Tanner
(74) *Attorney, Agent, or Firm* — Muncy, Geissler, Olds & Lowe, P.C.

(57) ABSTRACT

A drive handle and system for delivering an implant are disclosed. The drive handle includes a manual control unit, an electrical control unit and a transmission mechanism. The manual control unit is connected to the transmission mechanism to actuate the transmission mechanism to drive a delivery catheter for delivering the implant. The electrical control unit is connected to the transmission mechanism to actuate the transmission mechanism to drive the delivery catheter. The drive handle is switchable between a manual drive/control mode and an electrical drive/control mode to drive the delivery catheter to deliver the implant. The operation is simple, and the operating physician can take full advantage of the two modes to perform the surgical procedure based on his/her own operational preferences. This can (Continued)

result in higher surgical accuracy. Further, by providing these two modes, the apparatus has an increased the security and a reduced surgical risk.

14 Claims, 3 Drawing Sheets

(51) Int. Cl.
*A61F 2/966* (2013.01)
*A61F 2/46* (2006.01)

(56) References Cited

U.S. PATENT DOCUMENTS

| | | | |
|---|---|---|---|
| 2006/0119304 A1* | 6/2006 | Farritor | A61B 1/041 318/568.12 |
| 2008/0312536 A1* | 12/2008 | Dala-Krishna | A61B 8/12 600/459 |
| 2009/0099638 A1 | 4/2009 | Grewe | |
| 2010/0049313 A1* | 2/2010 | Alon | A61F 2/2436 623/2.11 |
| 2011/0213450 A1* | 9/2011 | Maclean | A61F 2/95 623/1.11 |
| 2012/0123528 A1 | 5/2012 | Knippel et al. | |
| 2012/0239142 A1 | 9/2012 | Liu et al. | |
| 2012/0305441 A1* | 12/2012 | Murray | A61M 25/002 206/570 |
| 2014/0180380 A1 | 6/2014 | Kelly | |
| 2014/0343670 A1* | 11/2014 | Bakis | A61F 2/2436 623/2.11 |

FOREIGN PATENT DOCUMENTS

| | | | |
|---|---|---|---|
| CN | 101961269 A | 2/2011 | |
| CN | 102573703 A | 7/2012 | |
| CN | 104173121 A | 12/2014 | |
| EP | 2349086 | 4/2010 | |
| WO | WO-2008124844 A1 * | 10/2008 | A61F 2/95 |
| WO | WO 2008124844 A1 | 10/2008 | |

* cited by examiner

DRIVING HANDLE FOR DELIVERING IMPLANT, AND DELIVERY SYSTEM

TECHNICAL FIELD

The present invention relates to the field of medical devices and, in particular, to a drive handle and system for delivering an implant.

BACKGROUND

Heart valve diseases are some of most frequently diagnosed cardiac diseases in China, and most of them are valve damage caused by rheumatic fever. In recent years, the aging population has led to an increasing incidence of valve degeneration (including calcification, mucoid degeneration, etc.) and valve damage caused by metabolic disorders in China.

Conventionally, heart valve surgery is an open-heart procedure conducted under general anesthesia, during which, following an incision made along the patient's sternum (sternotomy), the heart is stopped and blood flow is guided through a "heart-lung" bypass machine (extracorporeal circulation machine). Therefore, traditional heart valve surgery is a high injuries operation accompanied with obvious risks and may bring to the patient transient disturbances caused by emboli and other issues associated with the use of the extracorporeal circulation machine, such that a complete recovery typically requires a couple of months. In addition, for the elders and some special population groups, the trauma of the surgery is unbearable and the recovery needs more time and is sometime even impossible.

Minimally invasive intervention surgery offers a variety of advantages, including needlessness of sternotomy, minimal trauma and quick recovery for the patients. In the recent ten years, interventional therapies have shown a tendency to be able to cope with not only all diseases curable by internal and external treatments but also some diseases that the surgical treatments could not handle. After entering the twenty-first century, researches on interventional therapies for heart valve diseases such as percutaneous valve replacement technologies, have been experiencing a notable acceleration, and have evolved from experimental researches to small-scale clinical trials. And the interventional therapies for heart valve diseases are likely to have breakthroughs in technical "bottlenecks" to achieve large-scale clinical applications. This makes the technologies again a focus of research efforts in the field of interventional cardiology.

Valve implantation relies on a catheter for delivery of the stent. Currently, many manual delivery systems for a valve sent have been developed. Examples of such manual delivery systems include those disclosed in Chinese Patent Pub. No. CN101961269A assigned to Hangzhou Venus Medical Instrument Co., Ltd., Chinese Patent Pub. No. CN1961847A assigned to Wen Ning, Chinese Patent Pub. No. CN102573703A assigned to Medtronic, Inc. (the U.S.) and Chinese Patent Pub. No. CN101553190A assigned to Edwards Lifesciences Corp. (the U.S.). Such a manual delivery catheter generally comprises an inner shaft, an outer shaft, a valve stent and a push-pull mechanism. The inner shaft includes a guide tip and a connector for a valve stent. The valve stent is loaded on an intermediate section between the guide tip and the connector for the valve stent of the inner shaft and securely attached to the connector. The outer shaft shields over the inner shaft in order to cover the valve stent and is movable along the outer surface of the inner shaft. The push-pull mechanism is in operative connection with the inner shaft as well as with the outer shaft so as to deploy the valve stent.

However, these existing delivery catheters are operated with mechanical motions including rotating, advancing and retracting by manual means, which are tedious and laborious and prone to cause hand fatigue of the operating physicians. Additionally, the manual delivery operations impose high requirements on the operating physician and raise a considerable amount of risk in terms of faulty operations and inaccuracy of the operation which lead to deterioration in surgical performance.

U.S. Patent Pub. No. US20120239142A1 discloses an electric power-driven delivery system comprising a handle on which operator buttons are arranged for electrically controlling the advancement and retraction of the catheter for loading or deploying of the valve. This allows simple operation and reduces the operational burden on the physicians. However, the electric power-driven delivery of the catheter is associated with a great unknown risk for accidents which may lead to surgery failure and even patient deaths in severe cases.

SUMMARY OF THE INVENTION

It is an objective of the present invention to address the issues of operational complexity and a low security, arising from use of the conventional drive handles, by presenting a drive handle and system for delivering an implant, freely switchable between a manual drive mode and an electric drive mode for controlling and driving a catheter.

In order to address the above issues, the present invention provides a drive handle for delivering an implant, comprising a manual control unit, an electrical control unit and a transmission mechanism, the manual control unit being connected to the transmission mechanism to actuate the transmission mechanism to drive a delivery catheter for delivering the implant, the electrical control unit being connected to the transmission mechanism to actuate the transmission mechanism to drive the delivery catheter.

Optionally, in the drive handle, the transmission mechanism may comprise a motion conversion member, a lead screw and a motion transmission member, the lead screw having a first end connected to the motion conversion member and a second end connected to the motion transmission member, the motion conversion member being configured to receive a motion signal from the manual control unit for actuating the lead screw, the motion transmission member being configured to receive a motion signal from electrical control unit for actuating the lead screw.

Optionally, in the drive handle, the transmission mechanism may further comprise a support member, a displacement member disposed around the lead screw, and a connecting member disposed on the displacement member, the support member being configured to support and fix the lead screw, the lead screw being provided with an external thread for engaging with an internal thread of displacement member, the connecting member being configured to establish a connection between the lead screw and the delivery catheter.

Optionally, in the drive handle, the manual control unit may comprise a manual control member and a manual drive shaft connected to the manual control member.

Optionally, in the drive handle, electrical control unit may comprise a power supply, control buttons and a motor, the control buttons being configured to control a rotational direction of the motor, the power supply being configured to supply power to the control buttons and to the motor.

Optionally, in the drive handle, electrical control unit may further comprise a controller in electrical connection with the control buttons and the motor, the controller being configured to receive a direction command and a speed command from the control buttons and, control a rotational direction and a speed of the motor based on the direction command and the speed command.

The present invention also provides system for delivering an implant, comprising a delivery catheter and the drive handle for delivering an implant as defined above connected to the delivery catheter, the drive handle being configured to drive the delivery catheter so as to load or deploy the implant.

Optionally, in the system, the manual control unit, the electrical control unit, the transmission mechanism may be arranged within a first shell and a proximal end of the delivery catheter may be arranged within the first shell.

Optionally, in the system, the manual control unit, the electrical control unit and the transmission mechanism may be arranged within the first shell and the proximal end of the delivery catheter may be arranged within a second shell, wherein the first shell is detachably connected to the second shell, and wherein opposite sides of the first shell and the second shell are provided with displacement grooves, through which the connecting member for establishing the connection between the lead screw and the delivery catheter is detachably connected to the delivery catheter.

Optionally, in the system, the delivery catheter may comprise an inner shaft and an outer shaft disposed over a portion of the inner shaft, wherein the implant is loaded in a space between the outer shaft and the inner shaft.

Optionally, in the system, the delivery catheter may further comprise a stability shaft disposed over a portion of the outer shaft and a stability shaft mounting configured to fix the stability shaft.

Optionally, in the system, the inner shaft may comprise a guide tip and an a connector for the implant, wherein the implant is loaded over a section of the inner shaft between the guide tip and the connector for the implant, and wherein the implant has one end attached to the connector for the implant.

Optionally, in the system, the delivery catheter may further comprise an inner shaft mounting and an outer shaft mounting, the inner shaft mounting being configured to fix the inner shaft, the outer shaft mounting being configured to fix the outer shaft.

As noted above, the present invention provides the drive handle and delivery system for delivering an implant, the drive handle for delivering an implant comprising the manual control unit, the electrical control unit and the transmission mechanism, wherein the manual control unit is connected to the transmission mechanism to actuate the transmission mechanism to drive the delivery catheter, and the electrical control unit is connected to the transmission mechanism to actuate the transmission mechanism to drive the delivery catheter. Thus, the drive handle for delivering an implant is switchable between the manual and electrical drive/control modes to drive the delivery catheter to deliver the implant and improve security of the apparatus. The operation is simple, and the operating physician can perform the surgical procedure based on his/her own operational preferences, resulting in a reduced surgical risk.

BRIEF DESCRIPTION OF THE DRAWINGS

FIGS. 3a-3d shows a valve stent as the implant during release thereof, in which, FIG. 3a shows the valve stent that has not been deployed, FIGS. 3b and 3c show the valve stent that has been partially deployed, and FIG. 3d shows the valve stent that has been deployed.

In the figures, 1 denotes a drive handle for delivering an implant; 2, an inner shaft; 20, an inner shaft mounting; 21, an inner flush shaft; 210, an inner flush shaft mounting; 2b, a connector for implant; 2c, an implant loading section; 2d, a proximal end section of the inner shaft; 2a, a guide tip; 3, an outer shaft; 30, an outer shaft mounting; 4, a stability shaft; 40, a stability shaft mounting; 5, a delivery catheter; 6, a valve stent; 7, a first shell; 8, a second shell; 9, a hasp; 10, a manual control unit; 101, manual control member; 102, a manual drive shaft; 11, a electrical control unit; 110, a power supply; 111, a power supply contact; 112, a power supply switch; 113, a motor; 114, control buttons; 115, a controller; 12, a transmission mechanism; 120, a motion conversion member; 122, a motion transmission member; 123, a displacement member; 121, a lead screw; 124, a support member; and 125, connecting member.

DETAILED DESCRIPTION

The drive handle and delivery system proposed in this invention will be described in greater detail below with reference to the accompanying drawings and specific embodiments. Features and advantages of the invention will be more apparent from the following detailed description, and from the appended claims. Note that the figures are provided in a very simplified form not necessarily presented to scale, with the only intention of facilitating convenience and clarity in explaining the embodiments.

Figure 1:
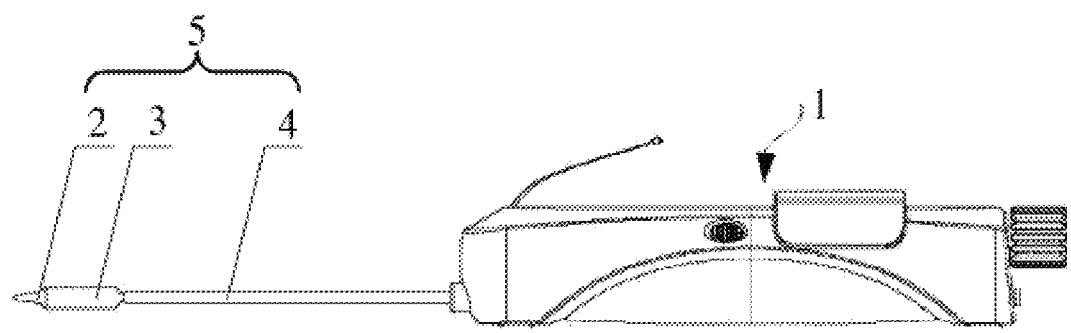
FIG. 1 is an elevation view of the implant delivery system according to a first embodiment of the present invention.
Figure 5:
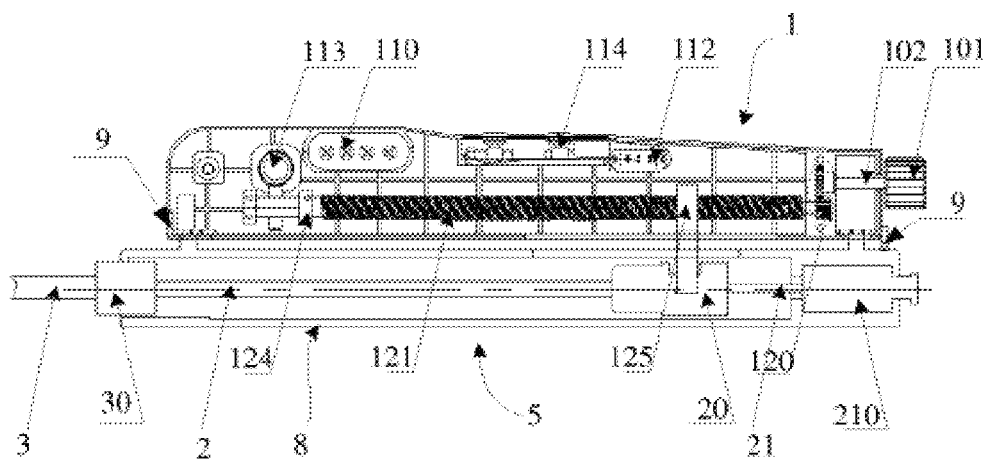
FIG. 5 is a partial cross-sectional view of the implant delivery system according to the second embodiment of the present invention.

Reference is now made to FIGS. 1 and 5, the implant delivery system of the present invention comprises a delivery catheter 5 and a drive handle 1 connected thereto for delivering an implant. The drive handle 1 drives the delivery catheter so that the implant is loaded or deployed. In some embodiments of the present invention, the delivery catheter 5 includes an inner shaft 2, an outer shaft 3 and a stability shaft 4.

According to the present invention, the delivery catheter 5 and the drive handle 1 may be disposed in two arrangements. In the first arrangement, the delivery catheter 5 and the drive handle 1 form an undetachable entity. In the second arrangement, the delivery catheter 5 and the drive handle 1 are separate parts coupled together in a detachable manner.

According to the arrangements of the delivery catheter 5 and drive handle 1, the implant delivery system of the present invention has the following two embodiments.

Embodiment 1

Reference is now made to FIG. 1, an elevation view of the implant delivery system according to a first embodiment of the present invention. As shown in FIG. 1, the system comprises: the delivery catheter 5 and the drive handle 1 that is connected to a proximal end of the delivery catheter 5. The drive handle 1 drives the delivery catheter 5 so as to allow loading and deploying of the implant.

Figure 2:
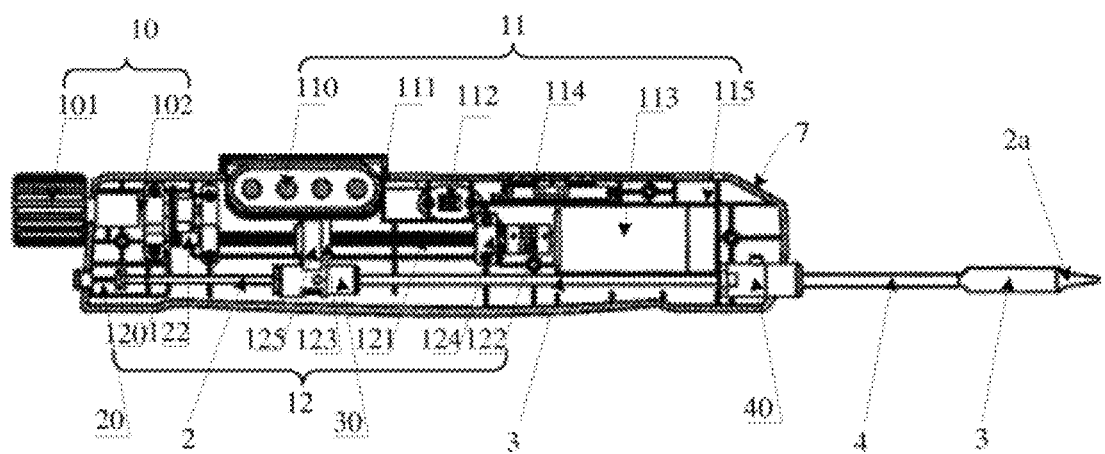
FIG. 2 is a partial cross-sectional view of the implant delivery system according to the first embodiment of the present invention.

Reference is now made to FIG. 2, a partial cross-sectional view of the implant delivery system according to the first embodiment of the present invention. FIG. 2 clearly shows a positional relationship between the drive handle 1 and the delivery catheter 5 with respect to each other and their constructions. The drive handle 1 includes a manual control unit 10, an electrical control unit 11 and a transmission mechanism 12. The manual control unit 10 is connected to the transmission mechanism 12 so as to allow the transmission mechanism 12 to drive the delivery catheter 5. The electrical control unit 11 is also connected to the transmission mechanism 12 so as to enable the transmission mechanism 12 to drive the delivery catheter 5. Additionally, the manual control unit 10, the electrical control unit 11 and the transmission mechanism 12 are all disposed in a first shell. The proximal end of the delivery catheter 5 is arranged within the first shell (note that, as used herein, the term "proximal end" refers to an end far away from a guide tip 2a of the inner shaft, while the "distal end" refers to an end close to the guide tip 2a of the inner shaft. Therefore, the proximal end of the delivery catheter refers to an end thereof located far away from the guide tip 2a of the inner shaft. Reference can be made to FIG. 1 for more details in this regard). Preferably, the delivery catheter 5 is connected to the drive handle 1 by connecting member 125. When a manual drive/control mode is selected, the manual control unit 10 actuates the transmission mechanism 12 so that the latter drives the delivery catheter 5. In case an electrical drive/control mode is selected, the electrical control unit 11 drives the transmission mechanism 12, thereby enabling the delivery of the implant by the delivery catheter 5. Thus, with the drive handle 1 of the present invention, the physician is allowed to select different modes for various practical needs. The operation is simple, and the physician can perform the surgical procedure based on his/her own operational preferences. In addition, since the drive handle 1 of the present invention can operate in two modes (i.e., the manual and electrical drive/control modes), in the event of one of the modes failing during an ongoing surgical procedure, it can be switched to the other mode to enable continuation of the procedure, thereby lowering the risk arising from driving the delivery catheter 5 in a single mode and hence increasing the security of the device.

Further, the transmission mechanism 12 includes a motion conversion member 120, a lead screw 121, a motion transmission member 122, a support member 124 and a displacement member 123 fitted around the lead screw 121. The lead screw 121 is connected to the motion conversion member 120 at one end and to the motion transmission member 122 at the other end. The motion conversion member 120 is configured to receive a motion signal for actuating the lead screw 121 from the manual control unit 10. The motion transmission member 122 is configured to receive another motion signal for actuating the lead screw 121 from the electrical control unit 11. The support member 124 is configured to support and mount the lead screw 121 and to limit the length of travel of the displacement member 123. The lead screw 121 is provided with an external thread that mates with an internal thread in the displacement member 123. The connecting member 125 is configured to establish a connection between the lead screw 121 and the delivery catheter 5. Preferably, the lead screw 121 is a screw rod. Here, the connection between the lead screw 121 and the proximal end of the delivery catheter refers to is established by means of the connecting member 125 that is disposed on the displacement member 123. More specifically, the connecting member 125 is connected to the outer shaft 3. Preferably, the displacement member is a nut. It is a matter of course that the displacement member may also be selected other than a nut in other specific embodiments. The connection between the lead screw 121 and the delivery catheter 5 includes, but is not limited to, to that established by the connecting member 125, and any otherwise established connection is also possible as long as it makes it possible that during axial movement of the displacement member 123 along the lead screw 121, there is a medium enabling the outer shaft 3 of the delivery catheter 5 to axially move relative to the inner shaft 2 and the stability shaft 4.

Further, the manual control unit 10 includes manual control member 101 and a manual drive shaft 102 connected to the manual control member 101.

Further, the electrical control unit 11 includes a power supply 110, control buttons 114 and a motor 113. The control buttons 114 control a rotational direction of the motor 113 and hence a transitional direction of the displacement member 123. The control buttons 114 and the motor 113 are powered by the power supply 110. Preferably, the motor is a direct current (DC) motor. More preferably, the electrical control unit 11 further includes a controller 115. The controller 115 receives direction and speed commands from the control buttons 114 and, based thereon, control the rotational direction and speed of the motor 113 and hence the transitional direction and speed of the displacement member 123. The power supply 110 supplies power to the controller 115 and the control buttons 114 via wires. Preferably, the motor 113 is a stepping motor. It will be readily appreciated that the electrical control unit 11 may be powered by a built-in power supply (e.g., the power supply 110) and corresponding supporting accessories (e.g., a power supply contact 111 and a power supply switch 112). The built-in power supply may be arranged in a power compartment (not shown) on the first shell 7 and is electrically connected to the power supply contact 111 which is also disposed within the compartment, with the power supply switch 112 being in electrical connection with the power supply contact 111 and the control buttons 114. Preferably, the built-in power supply is a disposable or rechargeable power supply. The present invention is not limited to any particular power supply, and a lithium, zinc-manganese, nickel-cadmium or other battery is possible. The electrical control unit 11 may also be powered by an external power supply and corresponding supporting accessories (e.g., the power supply switch 112). The power supply switch 112 is electrically connected to a power supply plug (not shown) and to the control buttons 114.

In this embodiment, the manual control unit 10, the automatic 1 land transmission mechanism 12 are all arranged in the first shell 7. Specifically, the power supply contact 111, control buttons 114 and controller 115 of the electrical control unit 11 are fixed on the first shell 7 by fitted and fixed into slots, while each of the power supply switch 112, the manual control unit 10 and the transmission mechanism 12 is fixed to the first shell 7 by screws.

Referring to FIGS. 1, 2 and 3a-3d, the delivery catheter 5 includes the inner shaft 2, the outer shaft 3 disposed over part of the inner shaft 2 and the stability shaft disposed over part of the outer shaft 3. The implant is loaded in a space between distal ends of the outer shaft 3 and the inner shaft 2. Specifically, the inner shaft 2 includes the guide tip 2a and a connector for the implant 2b. The implant is loaded around an implant loading section 2c between the guide tip 2a and the connector for the implant 2b, with its one end secured to the connector for the implant 2b. The "outer shaft 3 disposed over part of the inner shaft 2" is desired to be configured to allow a distal end of the outer shaft 3 to be close to the guide tip 2a during the delivery of the implant. The stability shaft 4 is provided mainly to prevent unwanted contact between the outer shaft 3 and the treated tissue when it is moved before the deployment of the implant. To this end, the stability shaft 4 covers as large part of the outer shaft 3 as possible. Meanwhile, during the delivery of the implant, the catheter 5 is required to pass through the aortic arch. This requires the delivery catheter 5 to have low bending stiffness and high flexibility. During the deployment of the implant, in order to fully release the implant, it is needed to move the outer shaft 3 toward the proximal end. This requires the outer shaft 3 not to be completely covered by the stability shaft 4. The length of the outer shaft 3 covered by the stability shaft 4 may be determined by those skilled in the art based on the geometry of the tissue and the type of the implant, in order to meet all of the foregoing requirements.

Furthermore, as shown in FIG. 2, the delivery catheter 5 further comprises an inner shaft mounting 20, an outer shaft mounting 30 and a stability shaft mounting 40. The inner shaft mounting 20 is disposed at a proximal end of the inner shaft 2 (i.e., the end thereof far away from the guide tip 2a) and is configured to secure the inner shaft 2. The outer shaft mounting 30 is disposed at a proximal end of the outer shaft 3 (i.e., the end thereof far away from the guide tip 2a) and is configured to secure the outer shaft 3. The outer shaft mounting 30 is provided with a lumen for passing through the inner shaft 2. The stability shaft mounting 40 is disposed at a proximal end of the stability shaft 4 (i.e., the end thereof far away from the guide tip 2a) and is configured to secure the stability shaft 4. The stability shaft mounting 40 is provided with a lumen for the passage of the outer shaft 3 therethrough. The inner shaft 2 is fixed to the first shell 7 by the inner shaft mounting 20. The outer shaft 3 is connected to the displacement member 123 by the outer shaft mounting 30 and the connecting member 125. The outer shaft mounting 30 is moveable relative to the first shell 7. The stability shaft 4 is fixed to the first shell 7 by the stability shaft mounting 40. Specifically, the proximal end of the inner shaft 2 is secured to the inner shaft mounting 20 which is, in turn, fitted and fixed into an inner shaft slot at a proximal end of the first shell 7. The proximal end of the stability shaft 4 is secured to the stability shaft mounting 40 which is, in turn, fitted and fixed into a stability shaft slot at a distal end of the first shell 7 (i.e., the end thereof close to the guide tip 2a).

Figure 3A:
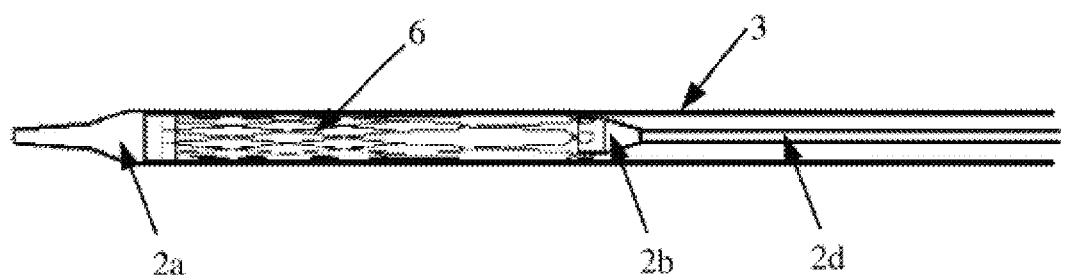
Figure 3B:
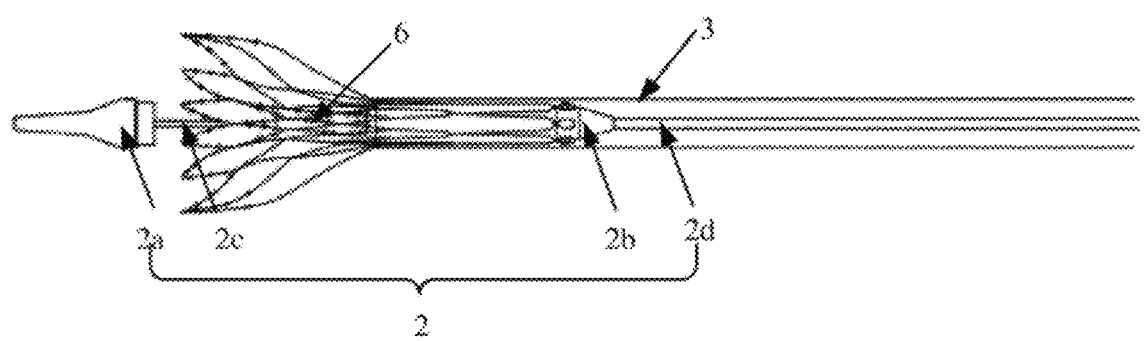
Figure 3C:
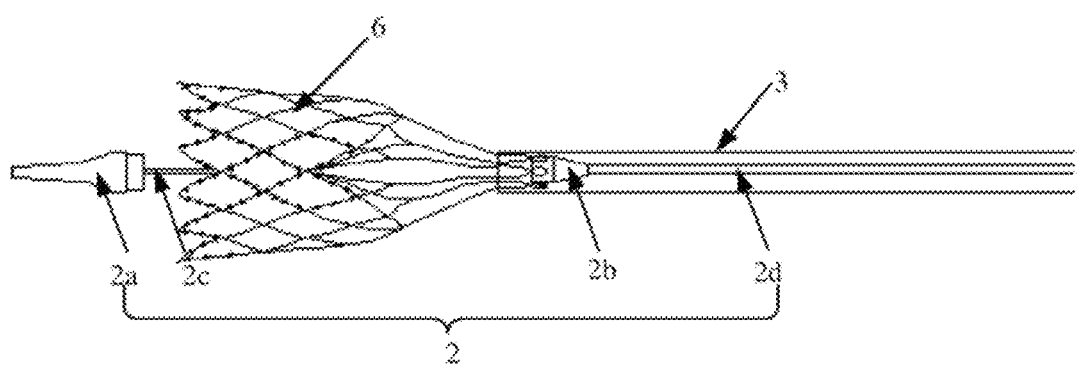
Figure 3D:
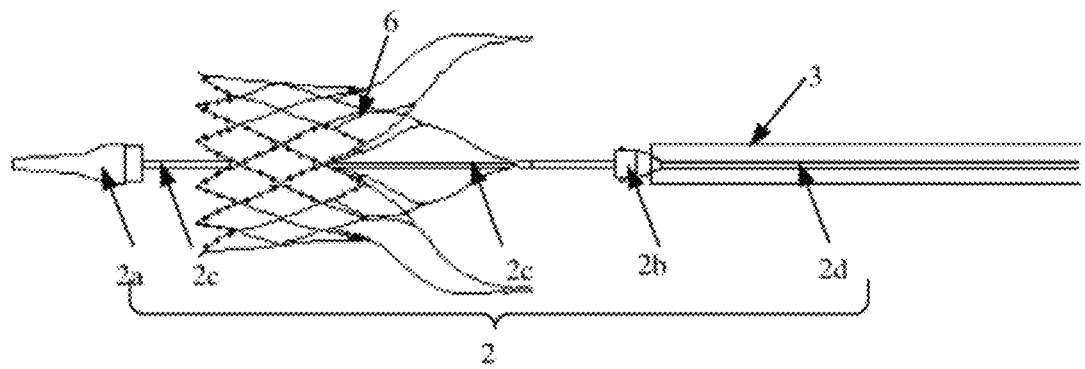

The process to deploy the implant by the delivery catheter 5 driven by the drive handle 1 will be better understood from the description set forth below in the context of a valve stent 6 being implemented as the implant, which is to be read in conjunction with FIGS. 3a-3d. FIG. 3a shows the valve stent 6 that has not been deployed. As clearly shown from FIG. 3a, the valve stent 6 is loaded around the section of the inner shaft 2 between the guide tip 2a and the connector for the implant 2b (i.e., the implant loading section 2c of the inner shaft 2), with a proximal end section 2d of the inner shaft connected at one end to the connector for the implant 2b and fixedly connected at the other end to the inner shaft mounting 20 by means of a threaded fit or an adhesive. The inner shaft mounting 20 is fitted and fixed into the inner shaft slot at the proximal end of the first shell 7 so that the inner shaft 2 is fixed as a whole relative to the drive handle 1. By doing this, it is also ensured that the valve stent 6 loaded on the connector for the implant 2b is fixed relative to the drive handle 1. The distal end of the outer shaft 3 is disposed over the valve stent 6 on the implant loading section 2c. Preferably, the distal end of the outer shaft 3 comes into contact with a proximal end face of the guide tip 2a at the distal end of the inner shaft 2, and the proximal end of the outer shaft 3 is fixed to the outer shaft mounting 30. In order to release the valve stent, regardless of whether in the manual or electrical drive/control mode, the outer shaft 3 is moved with the outer shaft mounting 30 relative to the drive handle 1, with the inner shaft 2 and the stability shaft 4 being fixed relative to the drive handle 1. Specifically, the lead screw 121 of the transmission mechanism 12 is connected at one end to the motor 113 in the electrical control unit 11 via the motion transmission member 122, so that when in the electrical drive/control mode, if the motor 113 rotates under the control of direction and speed parameters set by the control buttons 114, the rotation will be converted by the motion transmission member 122 and the lead screw 121 into axial movement of the displacement member 123. Under the action of the connecting member 125 that connects the displacement member 123 with the outer shaft mounting 30, the outer shaft 3 will then move along with the outer shaft mounting 30 axially relative to the inner shaft 2 and the stability shaft 4. When in the manual drive/control mode, rotation of the manual control member 101 can be transmitted to the lead screw 121 via both the manual drive shaft 102 and the motion conversion member 120 in the transmission mechanism 12, such that the lead screw 121 drives the displacement member 123 to move axially. As a result, the outer shaft 3 moves axially relative to the inner shaft 2 and the stability shaft 4. Reference can be made to FIGS. 3a-3d for the deployment of the valve stent 6 in both the manual and electrical drive/control modes. FIGS. 3b-3d show successive configurations of the valve stent 6 during the process in which the outer shaft 3 shown in FIG. 3a moves toward the proximal end of the drive handle, and the valve stent 6 is then accordingly deployed gradually from the delivery catheter 5. And states of the valve stent 6 are presented successively in FIGS. 3b-3d.

Obviously, loading of the valve stent in vitro may be achieved by choosing a direction opposite to that for deploying the valve stent by the control buttons 114, such that the outer shaft 3 and inner shaft 2 to move relative to each other in directions opposite to those for deploying the valve stent, or through manually rotating the manual control member in a direction opposite to that for deploying the valve stent.

While the embodiments herein are described in the context of the valve stent 6 (e.g., a heart valve stent) being implemented as the implant, those skilled in the art will appreciate that the delivery apparatus disclosed in the present invention may also be used to place other implants (e.g., vascular stents) than valve stents at their target sites in the body.

Figure 4:
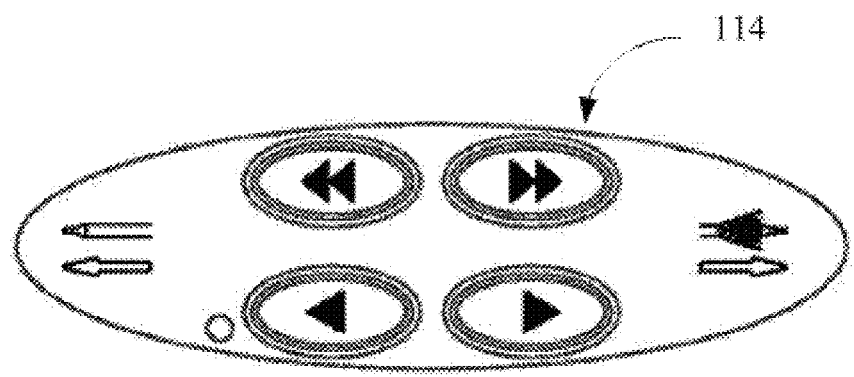
FIG. 4 is a top view of control buttons in an electrical control unit according to the first or second embodiment of the present invention.

FIG. 4 shows control buttons 114 each indicating a direction combined with a speed. The buttons in the first row are high-gear buttons (corresponding to higher speeds), while those in the second row are low-gear buttons (corresponding to lower speeds). Pressing a button marked with an arrow pointing to the right will cause the outer shaft 3 to retract to allow the release of the implant. When a button marked with an arrow pointing to the left is pressed, the outer shaft 3 will move in the opposite direction to allow the loading of the implant.

Embodiment 2

With combined reference to FIGS. 1 and 5, this second embodiment differs from Embodiment 1 in that a second shell 8 is further provided, wherein the manual control unit 10, the electrical control unit 11 and the transmission mechanism 12 are all disposed in the first shell 7, and the proximal end of the delivery catheter 5 is arranged in the second shell 8. The first shell 7 is connected to the second shell 8 in a detachable manner. Opposite sides of the first shell 7 and the second shell 8 are provided with displacement grooves, through which the connecting member 125 is detachably connected to the delivery catheter 5. The delivery catheter 5 includes the inner shaft 2 and the outer shaft 3 disposed over part of the inner shaft 2. The implant is loaded in a space between distal portions of the outer shaft 3 and the inner shaft 2. The delivery catheter 5 further comprises the inner shaft mounting 20 and the outer shaft mounting 30. The inner shaft mounting 20 is moveable relative to the second shell 8. The outer shaft mounting 30 is fixed at a distal end of the second shell 8. Preferably, the connecting member 125 is detachably connected to the inner shaft mounting 20 by means of a snap or other means. Preferably, the second shell 8 and the first shell 7 are connected together with a hasp 9.

Specifically, the inner shaft mounting 20 is disposed at the proximal end of the inner shaft 2 and is moveable relative to the second shell 8. More preferably, an inner flush shaft 21 is provided in the inner shaft and its proximal end is fixed into an inner flush shaft slot at a proximal end of the second shell 8 by means of an inner flush shaft mounting 210. The outer shaft mounting 30 at the proximal end of the outer shaft 3 is fixed into an outer shaft slot at the distal end of the second shell 8 and is provided with a lumen for the passage of the inner shaft 2 therethrough. In order to deploy the valve stent in the manual or electrical drive/control mode, the inner shaft mounting 20 is driven to move toward the distal end of the drive handle 1 such that the inner shaft 2 moves towards its distal end. In this embodiment, the drive handle 1 can be detached from the delivery catheter 5 as desired and to be reused, leading to lower surgical cost. In order to load the valve stent, the inner shaft 2 and the outer shaft 3 may be driven to move in opposite directions to those for deployment of the valve stent either by the manual control member 101 in an opposite direction or by the control buttons 114 with suitable direction parameters.

The embodiments herein are described in a progressive manner in which differences between the embodiments are emphasized. Reference may be made between the embodiments for details in their same or similar features.

In summary, the drive handle and system are provided in the present invention, the drive handle comprising the manual control unit, the electrical control unit and the transmission mechanism, the manual control unit being connected to the transmission mechanism to actuate the transmission mechanism to drive the delivery catheter, the electrical control unit being connected to the transmission mechanism to actuate the transmission mechanism to drive the delivery catheter. Thus, the drive handle of the present invention is switchable between the manual and electrical drive/control modes to drive the delivery catheter to deliver the implant. The operation is simple, and the operating physician can take full advantage of the two modes to perform the surgical procedure based on his/her own operational preferences. This can result in higher surgical accuracy. Further, by providing the two modes, the apparatus has an increased security and the surgical risk can be reduced.

The foregoing description presents merely some preferred embodiments of the present invention and is not intended to limit the scope of the invention in any sense. Any changes and modifications made by those skilled in the art in light of the disclosure herein are considered to fall within the scope defined by the appended claims.

What is claimed is:

1. A drive handle for delivering an implant, comprising a manual control unit, an electrical control unit and a transmission mechanism, wherein the manual control unit comprises a rotatable manual control member and a manual drive shaft connected to the manual control member, wherein the electrical control unit comprises a power supply, control buttons and a motor, the control buttons being configured to control a rotational direction of the motor;
wherein the transmission mechanism comprises a motion conversion member, a lead screw and a motion transmission member, the lead screw having a first end connected to the manual drive shaft of the manual control unit via the motion conversion member and a second end connected to the motor of the electrical control unit via the motion transmission member,
wherein a rotation of the rotatable manual control member of the manual control unit is transmitted to the motion conversion member to actuate the lead screw from the first end so as to drive a delivery catheter for delivering the implant in a manual control mode, and a rotation of the motor of the electrical control unit is transmitted to the motion transmission member to actuate the lead screw from the second end so as to drive the delivery catheter for delivering the implant in an electrical control mode,
wherein driving of the delivery catheter is freely switchable between the manual control mode and the electrical control mode.

2. The drive handle for delivering an implant of claim 1, wherein the transmission mechanism further comprises a support member, a displacement member disposed around the lead screw, and a connecting member disposed on the displacement member, the support member being configured to support and mount the lead screw, the lead screw being provided with an external thread for engaging with an internal thread of the displacement member, the connecting member being configured to establish a connection between the lead screw and the delivery catheter.

3. The drive handle for delivering an implant of claim 1, wherein the power supply supplies power to the control buttons and to the motor.

4. The drive handle for delivering an implant of claim 3, wherein the electrical control unit further comprises a controller in electrical connection with the control buttons and the motor, the controller being configured to receive a direction command and a speed command from the control buttons and to control a rotational direction and a speed of the motor based on the direction command and the speed command.

5. A system for delivering an implant, comprising a delivery catheter and a drive handle connected to the delivery catheter, the drive handle being configured to drive the delivery catheter so as to load or deploy the implant, wherein the drive handle comprises a manual control unit, an electrical control unit and a transmission mechanism, wherein the manual control unit comprises a rotatable manual control member and a manual drive shaft connected to the manual control member, wherein the electrical control unit comprises a power supply, control buttons and a motor, the control buttons being configured to control a rotational direction of the motor,
wherein the transmission mechanism comprises a motion conversion member, a lead screw and a motion transmission member, the lead screw having a first end connected to the manual drive shaft of the manual control unit via the motion conversion member and a second end connected to the motor of the electrical control unit via the motion transmission member, wherein a rotation of the rotatable manual control member of the manual control unit is transmitted to the motion conversion member to actuate the lead screw from the first end so as to drive a delivery catheter for delivering the implant in a manual control mode, and a rotation of the motor of the electrical control unit is transmitted to the motion transmission member to actuate the lead screw from the second end so as to drive the delivery catheter for delivering the implant in an electrical control mode, wherein driving of the delivery catheter is freely switchable between the manual control mode and the electrical control mode.

6. The system for delivering an implant of claim 5, wherein the manual control unit, the electrical control unit and the transmission mechanism are arranged within a first shell and wherein a proximal end of the delivery catheter is also arranged within the first shell.

7. The system for delivering an implant of claim 5, wherein the manual control unit, electrical control unit and the transmission mechanism are arranged within a first shell, wherein a proximal end of the delivery catheter is arranged within a second shell, wherein the first shell is detachably connected to the second shell, and wherein opposite sides of the first shell and the second shell are provided with displacement grooves, through which a connecting member for establishing a connection between the lead screw and the delivery catheter is detachably connected to the delivery catheter.

8. The system for delivering an implant of claim 5, wherein the delivery catheter comprises an inner shaft and an outer shaft disposed over a portion of the inner shaft, and wherein the implant is loaded in a space between the outer shaft and the inner shaft.

9. The system for delivering an implant of claim 8, wherein the delivery catheter further comprises a stability shaft disposed over a portion of the outer shaft and a stability shaft mounting configured to fix the stability shaft.

10. The system for delivering an implant of claim 8, wherein the inner shaft comprises a guide tip and a connector for the implant, wherein the implant is loaded over a section of the inner shaft between the guide tip and the connector for the implant, and wherein the implant has one end attached to the connector for the implant.

11. The system for delivering an implant of claim 8, wherein the delivery catheter further comprises an inner shaft mounting and an outer shaft mounting, the inner shaft mounting being configured to fix the inner shaft, the outer shaft mounting being configured to fix the outer shaft.

12. The system for delivering an implant of claim 5, wherein the transmission mechanism further comprises a support member, a displacement member disposed around the lead screw, and a connecting member disposed on the displacement member, the support member being configured to support and mount the lead screw, the lead screw being provided with an external thread for engaging with an internal thread of the displacement member, the connecting member being configured to establish a connection between the lead screw and the delivery catheter.

13. The system for delivering an implant of claim 5, wherein the power supply supplies power to the control buttons and to the motor.

14. The system for delivering an implant of claim 13, wherein the electrical control unit further comprises a controller in electrical connection with the control buttons and the motor, the controller being configured to receive a direction command and a speed command from the control buttons and to control the rotational direction and a speed of the motor based on the direction command and the speed command.

* * * * *